United States Patent
McCabe et al.

(10) Patent No.: US 7,751,890 B2
(45) Date of Patent: Jul. 6, 2010

(54) SELF-DIAGNOSTIC METHOD AND SYSTEM FOR IMPLANTABLE CARDIAC DEVICE

(75) Inventors: Aaron McCabe, Minneapolis, MN (US); David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1278 days.

(21) Appl. No.: 10/890,810

(22) Filed: Jul. 14, 2004

(65) Prior Publication Data

US 2006/0015148 A1  Jan. 19, 2006

(51) Int. Cl.
*A61N 1/00* (2006.01)
*A61B 5/04* (2006.01)

(52) U.S. Cl. .......................... 607/27; 600/510

(58) Field of Classification Search .................. 607/9, 607/17–20, 27, 28; 600/483, 484, 513, 547, 600/510
See application file for complete search history.

(56) References Cited

U.S. PATENT DOCUMENTS

| | | | |
|---|---|---|---|
| 4,088,139 A * | 5/1978 | Auerbach ................... 607/27 |
| 4,585,004 A | 4/1986 | Brownlee | |
| 5,040,533 A | 8/1991 | Fearnot | |
| 5,127,401 A | 7/1992 | Grevious et al. | |
| 5,265,602 A | 11/1993 | Anderson et al. | |
| 5,324,310 A | 6/1994 | Greeninger et al. | |
| 5,331,966 A * | 7/1994 | Bennett et al. ............. 600/508 |
| 5,366,487 A | 11/1994 | Adams et al. | |
| 5,423,871 A | 6/1995 | Hoegnelid et al. | |
| 5,549,646 A | 8/1996 | Katz et al. | |
| 5,682,902 A | 11/1997 | Herleikson | |
| 5,776,168 A | 7/1998 | Gunderson | |
| 5,987,352 A | 11/1999 | Klein et al. | |
| 6,115,630 A | 9/2000 | Stadler et al. | |
| 6,161,042 A | 12/2000 | Hartley et al. | |
| 6,230,059 B1 | 5/2001 | Duffin | |
| 6,236,882 B1 | 5/2001 | Lee et al. | |
| 6,275,733 B1 * | 8/2001 | Park et al. ................... 607/18 |
| 6,317,633 B1 | 11/2001 | Jorgenson et al. | |

(Continued)

FOREIGN PATENT DOCUMENTS

DE  4405827  6/1995

(Continued)

OTHER PUBLICATIONS

Mazur, Alexander, "Functional similarity between electrograms recorded from an implantable cardioverter defibrillator emulator and the surface electrocardiogram", *PACE*, vol. 24, (Jan. 2001), 34-40.

(Continued)

*Primary Examiner*—Mark W Bockelman
(74) *Attorney, Agent, or Firm*—Schwegman, Lundberg & Woessner, P.A.

(57) ABSTRACT

A self-diagnostic system for an implantable cardiac device such as a pacemaker, cardioverter, or resynchronization device which utilizes a subcutaneous ECG channel is described. The subcutaneous ECG channel allows the device to, in real time and independent of the standard pacing and sensing circuitry, verify the presence of pacing spikes, chamber senses, and other device outputs and hence establish and verify device integrity.

23 Claims, 3 Drawing Sheets

U.S. PATENT DOCUMENTS

| | | | |
|---|---|---|---|
| 6,324,421 B1 | 11/2001 | Stadler et al. | |
| 6,334,071 B1 | 12/2001 | Lu | |
| 6,347,245 B1 | 2/2002 | Lee et al. | |
| 6,397,100 B2 | 5/2002 | Stadler et al. | |
| 6,405,083 B1 | 6/2002 | Rockwell et al. | |
| 6,477,404 B1 | 11/2002 | Yonce et al. | |
| 6,493,586 B1 * | 12/2002 | Stahmann et al. | 607/27 |
| 6,496,715 B1 | 12/2002 | Lee et al. | |
| 6,658,283 B1 | 12/2003 | Bornzin et al. | |
| 6,990,375 B2 * | 1/2006 | Kloss et al. | 607/20 |
| 7,107,093 B2 * | 9/2006 | Burnes | 600/509 |
| 7,203,535 B1 | 4/2007 | Hsu et al. | |
| 7,212,849 B2 | 5/2007 | Zhang et al. | |
| 7,228,176 B2 | 6/2007 | Smith et al. | |
| 7,299,086 B2 | 11/2007 | McCabe et al. | |
| 2002/0016548 A1 | 2/2002 | Stadler et al. | |
| 2002/0026122 A1 | 2/2002 | Lee et al. | |
| 2002/0049474 A1 | 4/2002 | Marcovecchio et al. | |
| 2002/0065539 A1 | 5/2002 | Von Arx et al. | |
| 2002/0143262 A1 | 10/2002 | Bardy | |
| 2002/0143372 A1 | 10/2002 | Snell et al. | |
| 2003/0004552 A1 | 1/2003 | Plombon et al. | |
| 2004/0215240 A1 * | 10/2004 | Lovett et al. | 607/4 |
| 2004/0230229 A1 * | 11/2004 | Lovett et al. | 607/4 |
| 2005/0010257 A1 | 1/2005 | Lincoln et al. | |
| 2005/0197674 A1 | 9/2005 | McCabe et al. | |
| 2006/0095083 A1 | 5/2006 | Zhang et al. | |
| 2007/0167849 A1 | 7/2007 | Zhang et al. | |
| 2007/0179392 A1 | 8/2007 | Zhang | |
| 2008/0051672 A1 | 2/2008 | McCabe et al. | |

FOREIGN PATENT DOCUMENTS

| | | |
|---|---|---|
| EP | 0308536 A1 | 3/1989 |
| EP | 0784996 A1 | 7/1997 |
| WO | WO-2005089643 A1 | 9/2005 |
| WO | WO-2006049767 A1 | 5/2006 |

OTHER PUBLICATIONS

Theres, Heinz, et al., "Electrogram signals recorded from acute and chronic pacemaker implantation sites in pacemaker patie", *PACE*, vol. 21, Part 1, (Jan. 1998), 11-17.

Zhang, Yi, "Rejection of Noises Caused by Postural Changes During Acute Myocardial Infarction Detection", U.S. Appl. No. 11/275,800, date mailed Jan. 30, 2006, 60 Pages.

"U.S. Appl. No. 10/795,126 Non final office action mailed Jan. 25, 2007", 17 pgs.

"U.S. Appl. No. 10/795,126 Notice of allowance mailed Jul. 9, 2007", 10 pgs.

"U.S. Appl. No. 10/795,126 Response filed Apr. 25, 2007 to Non final office action mailed Jan. 25, 2007", 11 pgs.

"U.S. Appl. No. 10/975,166 Notice of allowance mailed Dec. 21, 2006", 17 pgs.

* cited by examiner

SELF-DIAGNOSTIC METHOD AND SYSTEM FOR IMPLANTABLE CARDIAC DEVICE

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used in treatment of cardiac conduction disorders in order to improve the coordination of cardiac contractions, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities. Any device with a pacing functionality will be referred to herein simply as a pacemaker regardless of other functions it may be capable of performing.

Cardiac rhythm management devices such as described above monitor the electrical activity of heart via one or more sensing channels so that pacing pulses or defibrillation shocks can be delivered appropriately. Such sensing channels include implanted leads which have electrodes disposed internally near the heart, which leads may also be used for delivering pacing pulses or defibrillation shocks. The signals generated from the sensing channels are intra-cardiac electrograms and reflect the time course of depolarization and repolarization as the heart beats, similar to a surface electrocardiogram (ECG). A device may also employ other types of sensing modalities such as an accelerometer and/or a minute ventilation sensor for measuring the patient's exertion level. In rate-adaptive pacing modes, the pacing rate is adjusted in accordance with a measured exertion level.

Various means are commonly used to monitor the condition of the sensing and pacing systems of an implantable device after implantation. Clinicians traditionally utilize the surface ECG in a follow-up setting to verify the functionality of an implantable cardiac device. The surface ECG offers a far-field view of cardiac electrical activity, producing larger and higher fidelity signals than available from most device electrograms, which aids in verifying capture of the heart by pacing pulses. Additionally, the surface ECG provides the only independent view of the implanted device behavior. This can be critical when reconciling confusing device behavior or diagnosing a malfunctioning device or broken lead. Because of this, many clinicians insist on a surface ECG to confirm device operation.

DETAILED DESCRIPTION

Implantable cardiac devices may incorporate one or more subcutaneously disposed electrodes (e.g., on the surface of the device housing) into a sensing channel for generating an electrogram signal, referred to herein as a subcutaneous ECG. A subcutaneous ECG is more similar in its morphology characteristics to a surface ECG than is an intra-cardiac electrogram. The electrogram signals generated from the sensing channels of an implanted device, whether an intra-cardiac electrogram or a subcutaneous ECG, may be transmitted wirelessly to an external device where they can be displayed and analyzed in much the same manner as a surface electrocardiogram (ECG). The present disclosure relates to a system and method by which an implantable device may utilize the subcutaneous ECG for self-diagnostic purposes. The subcutaneous ECG is an independent sensing channel by which the device may monitor its input signals and pacing outputs in real-time. In an exemplary embodiment, such a self-diagnostic system is implemented by appropriate programming of the controller of an implantable cardiac rhythm management device as described below.

1. Exemplary Implantable Device Description

Figure 1:
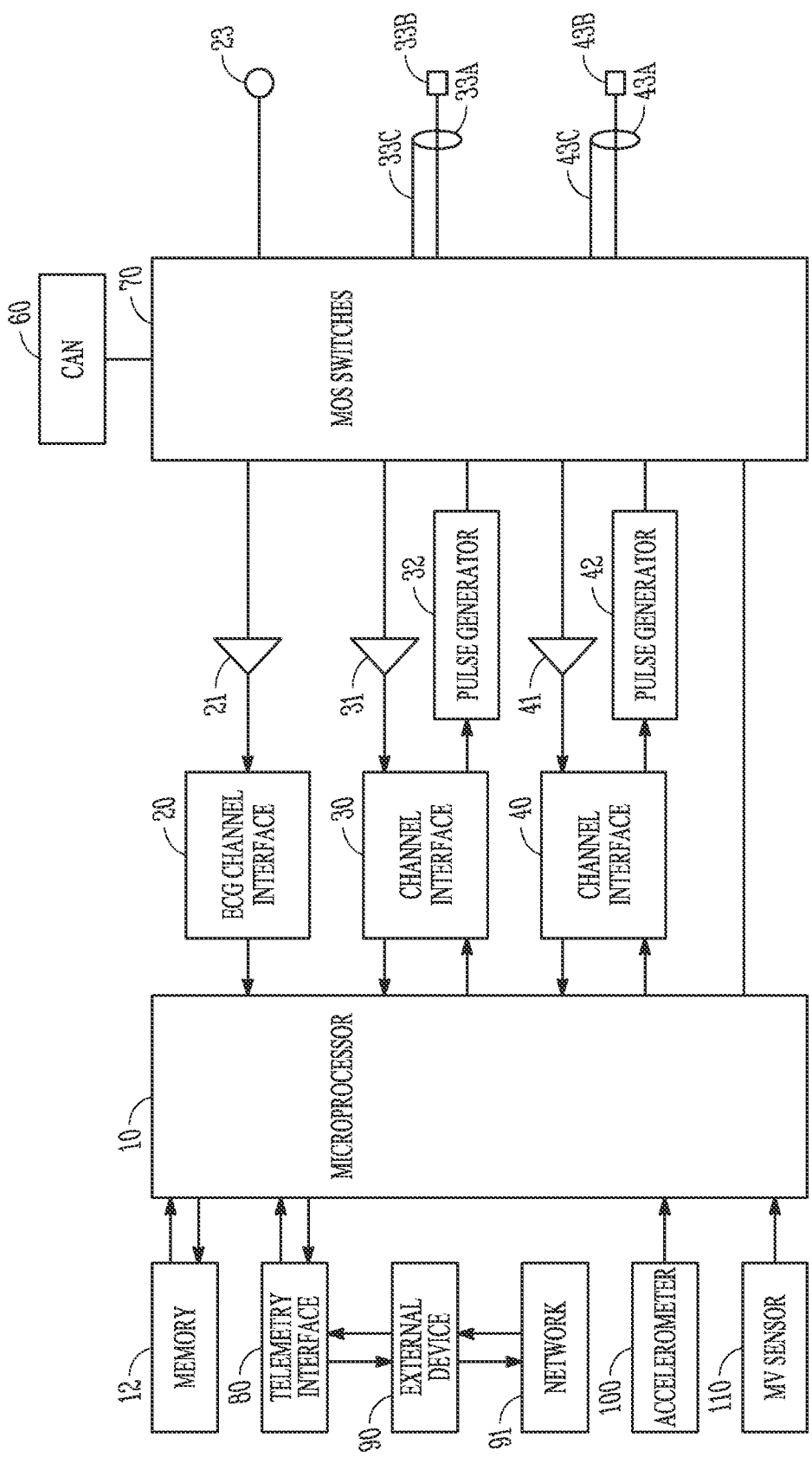
FIG. 1 is a block diagram of an exemplary cardiac rhythm management device for practicing the present invention.

Cardiac rhythm management devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. A block diagram of an exemplary implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external device 90 via a wireless telemetry link. The external device 90 may be an external programmer which can be used to program the implantable device as well as receive data from it or a remote monitoring unit. The external device 90 may also be interfaced to a patient management network 91 enabling the implantable device to transmit data and alarm messages to clinical personnel over the network. The network connection between the external device 90 and the patient management network 91 may be implemented by, for example, an internet connection, over a phone line, or via a cellular wireless link.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In an example configuration, one sensing/pacing channel includes ring electrode 43a and tip electrode 43b of bipolar lead 43c, sense amplifier 41, pulse generator 42, and a channel interface 40 while another sensing/pacing channel includes ring electrode 33a and tip electrode 33b of bipolar lead 33c, sense amplifier 31, pulse generator 32, and a channel interface 30. The channels may be configured as either atrial or ventricular channels, where the sensing channels then generate intra-cardiac electrograms from an atrium and a ventricle. An electrogram signal used to approximate a surface ECG for self-diagnostic purposes is preferably obtained by a dedicated sensing channel. Such a dedicated subcutaneous ECG sensing channel is shown in the figure as made up of a channel interface 20, sense amplifier 21, and electrode 23 which can be disposed subcutaneously for generating a subcutaneous ECG. In one embodiment, the ECG electrode 23 is mounted on the device housing. Also, more than one subcutaneous ECG electrodes may be provided. The switch matrix may configure the sensing vector of a subcutaneous ECG channel by referencing the electrode 23 to the device housing or can or to other subcutaneous electrodes. An embodiment of a subcutaneous ECG sensing channel which utilizes two electrodes on the device header and the device housing is described in co-pending U.S. patent application Ser. No. 10/795,126, filed on Mar. 5, 2004 and hereby incorporated by reference in its entirety.

The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates chamber sense signals (i.e., atrial or ventricular senses) when voltages sensed by the electrodes of a particular channel exceed a specified threshold. A ventricular sense would correspond to an R wave on an ECG, and an atrial sense would correspond to a P wave. The controller 10 interprets sense signals from the sensing channels in order to detect arrhythmias and to control the delivery of paces in accordance with a pacing algorithm that employs such senses to trigger or inhibit pacing. The electrogram signals can also be digitized and recorded (i.e., stored in memory) by the controller and then either transmitted via a telemetry link 80 to an external device or maintained in memory or other storage medium for later transmission. The patient's cardiac activity may thus be observed in real-time or over a selected historical period.

Also interfaced to the controller are a minute ventilation sensor 110 and an accelerometer 100 for use in measuring a parameter related to the patient's exertion level and adjusting the pacing rate of the device accordingly in rate-adaptive pacing modes. The accelerometer and minute ventilation sensor produce a signal which approximates the patient's exertion level by measuring body activity and respiratory volume rate, respectively. The minute ventilation sensor measures the respiratory volume by injecting bursts of excitation current between excitation electrodes and measuring a transthoracic voltage drop to derive a signal proportional to the transthoracic impedance. A particular minute ventilation sensor is described in U.S. Pat. No. 6,161,042, assigned to the assignee of the present application and hereby incorporated by reference in its entirety.

2. Self-Diagnostic System

Described herein is a self-diagnostic system for an implantable cardiac device such as a pacemaker, cardioverter, or resynchronization device which utilizes a subcutaneous ECG channel such as illustrated in FIG. 1. The subcutaneous ECG channel allows the device to, in real time and independent of the standard pacing and sensing circuitry, verify the presence of pacing spikes and other device outputs and hence establish and verify device integrity. The state of the pacing system may be diagnosed and verified that it is operating as expected by sensing features such as (but not limited to) pacing spikes, chamber sense signals, PR and RP intervals, and minute ventilation signals.

An exemplary device which implements such a self-diagnostic system includes one or more sensing channels for sensing intrinsic cardiac activity and generating intra-cardiac electrogram signals, a sensing channel incorporating a subcutaneous electrode for generating a subcutaneous ECG signal, a pacing channel for pacing a cardiac chamber, a controller for receiving sensing signals and controlling the delivery of pacing pulses in accordance with a programmed mode, and programming of the controller to detect pacing outputs in the subcutaneous ECG signal and set an alarm flag if a programmable number of paces fail to be detected. In addition to or instead of detecting pacing pulses, the controller may also be programmed to cross-check chamber senses in the subcutaneous ECG channel and one or more sensing channels which generate intra-cardiac electrogram signals and set an alarm flag if a programmable number of cross-checks fail. Another check on the intra-cardiac sensing channels may be performed by the controller computing various intervals between chamber senses, such as PR or RP intervals, as detected in both the subcutaneous ECG channel and the intra-cardiac sensing channel. If the discrepancy exceeds a programmable limit, the alarm flag may then be set.

Another diagnostic modality which may be performed by a self-diagnostic system deals with the minute ventilation sensor. The minute ventilation sensor outputs bursts of excitation current for measuring trans-thoracic impedance, and the controller may be programmed to detect excitation current bursts in the subcutaneous ECG signal and set an alarm flag if a programmable number of such bursts fail to be detected. The system may further test the minute ventilation sensor by cross-checking the exertion levels measured by both the minute ventilation sensor and an accelerometer. An alarm flag is then set if there is a discrepancy between the two measurements which exceeds a programmable limit.

In one embodiment, if the diagnostic system determines that the device is not operating adequately such as determined by failure to detect pacing pulses in the surface ECG or by discrepancies between the subcutaneous ECG and signals received from the intra-cardiac sensing channels, the device may be programmed to go into a fallback or safety mode. Such a fallback mode may entail, for example, asynchronous pacing, no pacing, or switching from bipolar to unipolar pacing. In another embodiment, the device is programmed so that a determination of inadequate operation causes an alarm flag to be set. The alarm flag may then be transmitted via the device's telemetry link to an external programmer during a subsequent communications session and/or transmitted to an external device which may then communicate the information to a patient management network.

Figure 2:
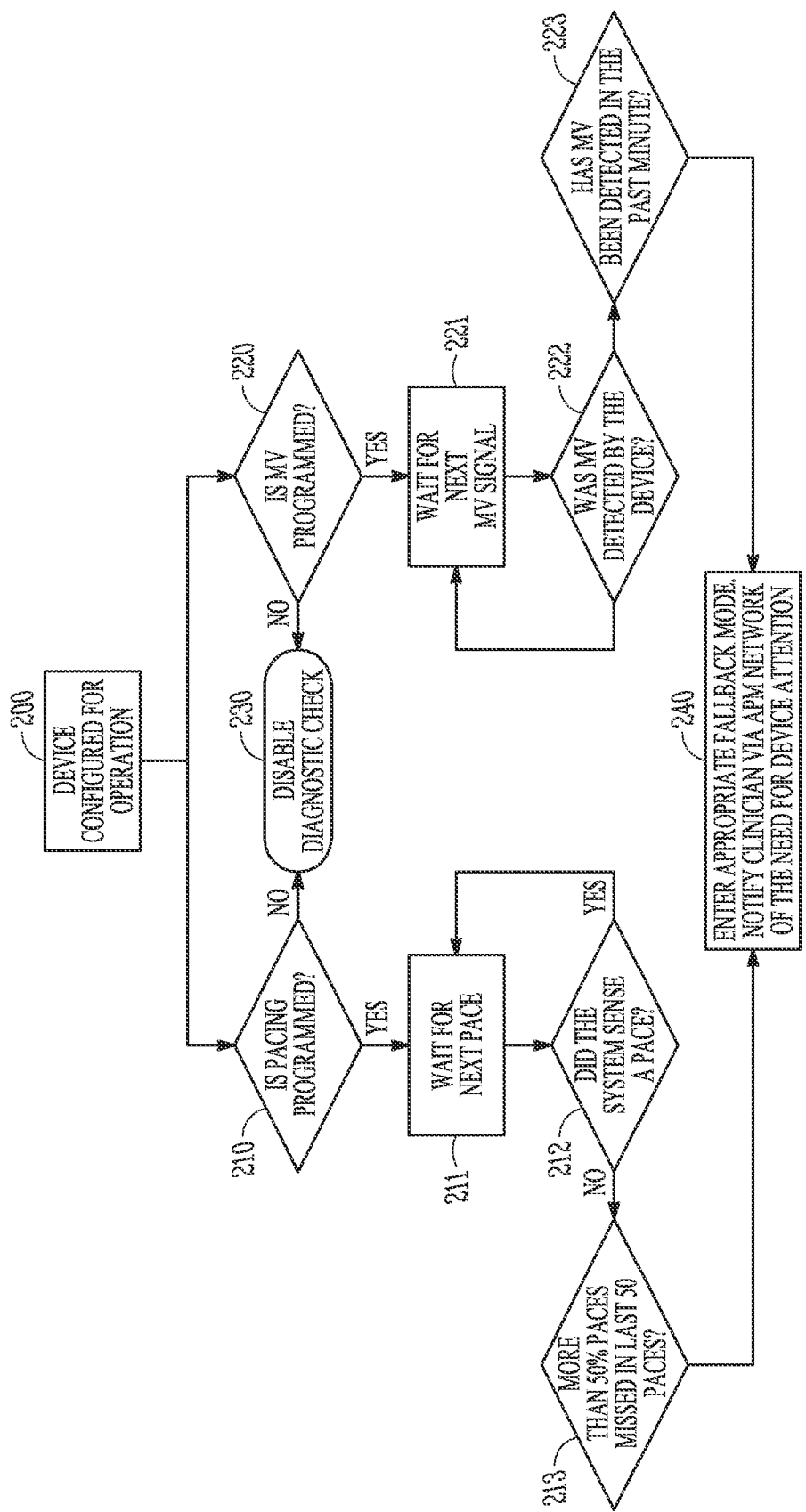
FIG. 2 illustrates an exemplary self-diagnostic algorithm.

FIG. 2 shows a high-level flowchart diagram of an exemplary algorithm that could be executed by an implantable device in order to provide an independent diagnosis of device operation. This particular example shows how pacing and minute ventilation can be both be simultaneously detected and measured for performance. If signals from the pacing and minute ventilation systems are appropriately detected, then the device continues to sense these signals for subsequent events. If a suitable number of paces or MV signals are not detected in a certain timeframe, then the device declares a fault, enters the appropriate fallback mode, and sets an alarm flag. The diagnostic algorithm may be used as an initial calibration procedure in order to check the device shortly after implantation where the algorithm is executed upon receiving a command to do so from an external programmer. The algorithm may also be executed continuously or periodically by the device as an automatic self-calibration procedure. Referring to the figure, once the device has been programmed with pacing parameters and/or minute ventilation (MV) activated at step 200, it enters separate routines for sensing the pacing and MV signals from the pacemaker outputs using the subcutaneous ECG channel. The device checks to see if pacing or MV sensing is programmed at steps 210 and 220, respectively, and disables diagnostic checking for one or both of these systems at step 230 as appropriate. If diagnostic checking for pacing is not disabled, the device waits for the next pace at step 211 and checks to see if the pace was detected by the subcutaneous ECG channel at step 212. In this example, if more than 50% of paces have gone undetected by the ECG channel in the last 50 paces as determined at step 213, the device enters its fallback mode at step 240 which includes setting an alarm flag for notifying a clinician during a programming session or via the patient management network of the device's need for attention. If diagnostic checking for MV sensing is not disabled, the device waits for the next MV signal (i.e., the excitation current burst) at step 221 and checks to see if the MV signal was detected in the ECG channel at step 222. If no MV activity has been detected in the past minute as determined at step 223, the device enters the fallback mode at step 240.

Figure 3:
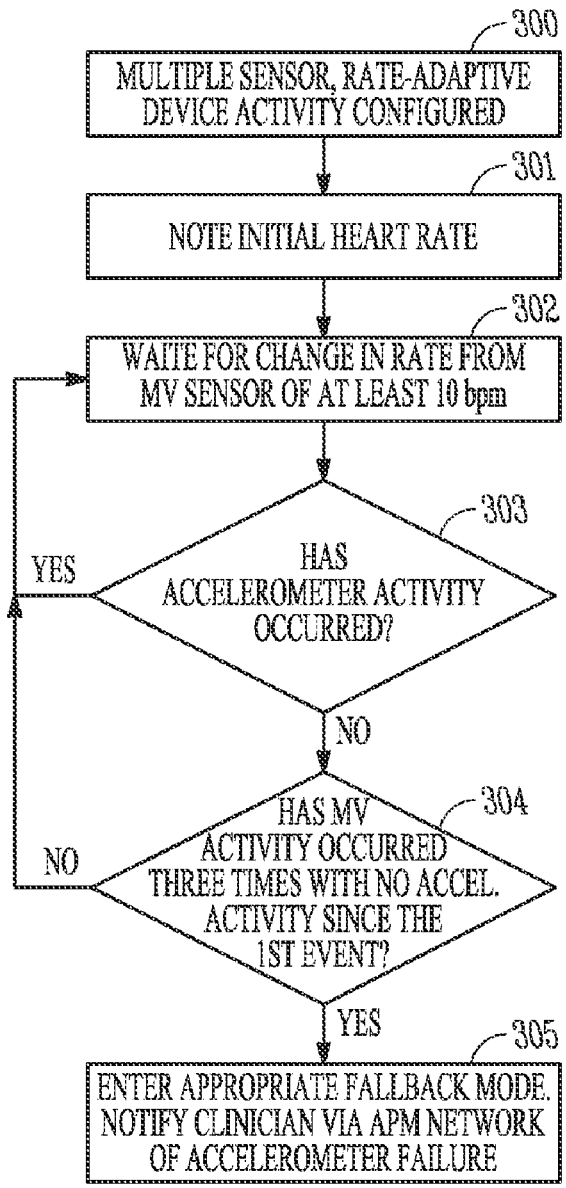
FIG. 3 illustrates an exemplary algorithm for cross-checking exertion level sensors.

FIG. 3 shows an example of a different type of diagnostic check to verify the operation of the accelerometer in a blended sensor system. Many pacemakers employ a blended sensor system to adjust the pacing rate based upon a combination of a minute ventilation sensor and an accelerometer. The two sensors together produce a better rate response to physical exertion than either alone. The algorithm in FIG. 3 shows an exemplary method for detecting a failed accelerometer based upon the activity of the minute ventilation system. Most often, both sensors produce a signal when there is physical activity. If the MV sensor indicates a change in rate over a time period, then the system also checks to verify activity on the accelerometer. There are rare situations, such as riding a stationary exercise bike, where the MV will be the dominant rate control sensor without the effect of the accelerometer. To account for this, the system waits for a programmable number of indications (e.g., three) of significantly higher rate driven by MV without any accelerometer activity throughout the entire duration since the first MV activity. In this case, the device detects the accelerometer as failed, enters a fallback mode for the rate adaptive functions, and sets an alarm flag so that a clinician is notified during a programming session and/or via a patient management network. Referring to the figure, the device is configured to use an accelerometer and MV sensor at step 300, and the initial MV sensor-indicated heart rate is noted at step 301. The device next waits for a change in the sensor-indicated rate from the MV sensor of some predetermined extent (e.g., at least 10 bpm) at step 302. If corresponding accelerometer activity has also occurred as determined at step 303, the device returns to step 302. If no corresponding accelerometer activity has occurred, the device checks to see if a programmable number of events (e.g., three) of MV activity with no corresponding accelerometer activity have occurred at step 304. If so, the device enters the fallback mode at step 305.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
   one or more intra-cardiac sensing channels for sensing intrinsic cardiac activity and generating intra-cardiac electrogram signals;
   a sensing channel incorporating a subcutaneous electrode for generating a subcutaneous ECG signal wherein the subcutaneous electrode is mounted on an implantable housing for the device;
   a pacing channel for pacing a cardiac chamber;
   a controller for receiving sensing signals and controlling the delivery of pacing pulses in accordance with a programmed mode; and,
   wherein the controller is programmed to detect chamber senses in the subcutaneous ECG and intra-cardiac electrogram signals, cross-check the chamber senses detected in the subcutaneous ECG signal and the intra-cardiac electrogram signal to determine whether a chamber sense is detected in one signal but not the other, and set an alarm flag if a discrepancy is found to exist.

2. The device of claim 1 wherein the controller is programmed to detect pacing outputs in the subcutaneous ECG signal and set an alarm flag if a programmable number of paces fail to be detected.

3. The device of claim 2 wherein the controller is programmed to enter a fallback mode if the alarm flag is set.

4. The device of claim 3 wherein the fallback mode includes reverting to asynchronous pacing.

5. The device of claim 3 wherein the fallback mode causes cessation of pacing by the device.

6. The device of claim 1 wherein the controller is programmed to:
cross-check chamber senses in the subcutaneous ECG channel and one or more sensing channels which generate intra-cardiac electrogram signals; and,
set an alarm flag if a programmable number of cross-checks fail.

7. The device of claim 6 wherein the cross-checking of chamber senses includes measurement of intervals between chamber senses in the subcutaneous ECG channel and intra-cardiac sensing channel.

8. The device of claim 1 further comprising:
a minute ventilation sensor which outputs bursts of excitation current for measuring trans-thoracic impedance; and,
wherein the controller is programmed to detect excitation current bursts in the subcutaneous ECG signal and set an alarm flag if a programmable number of such bursts fail to be detected.

9. The device of claim 1 further comprising:
an accelerometer for detecting body activity;
a minute ventilation sensor which outputs bursts of excitation current for measuring trans-thoracic impedance; and,
wherein the controller is programmed to cross-check the activity of the accelerometer and minute ventilation sensor and set an alarm flag if a discrepancy exists.

10. The device of claim 1 further comprising:
a telemetry interface communicating with an external device connected to a patient management network; and,
wherein the controller is programmed to communicate the setting of the alarm flag to the patient management network.

11. The device of claim 1 wherein the controller is programmed to periodically detect device events in the subcutaneous ECG signal and set an alarm flag if a discrepancy is found to exist.

12. The device of claim 1 further comprising a telemetry interface and wherein the controller is programmed to detect device events in the subcutaneous ECG signal and set an alarm flag if a discrepancy is found to exist upon receiving a command to do so via the telemetry interface.

13. A method for operating a cardiac rhythm management device, comprising:
sensing cardiac activity via an intra-cardiac sensing channel incorporating an intra-cardiac electrode;
recording a subcutaneous ECG signal from a subcutaneous sensing channel incorporating a subcutaneous electrode wherein the subcutaneous electrode is mounted on an implantable housing for the device;
delivering pacing pulses to a cardiac chamber in accordance with a programmed mode; and,
detecting chamber senses in the subcutaneous ECG and intra-cardiac electrogram signals, cross-checking the chamber senses detected in the subcutaneous ECG signal and the intra-cardiac electrogram signal to determine whether a chamber sense is detected in one signal but not the other, and setting an alarm flag if a discrepancy is found to exist.

14. The method of claim 13 further comprising detecting pacing outputs in the subcutaneous ECG signal and setting an alarm flag if a programmable number of paces fail to be detected.

15. The method of claim 14 further comprising entering a fallback mode if the alarm flag is set.

16. The method of claim 15 wherein the fallback mode includes reverting to asynchronous pacing.

17. The method of claim 15 wherein the fallback mode causes cessation of pacing by the device.

18. The method of claim 15 wherein the fallback mode includes switching from bipolar to unipolar pacing.

19. The method of claim 13 further comprising:
cross-checking chamber senses in the subcutaneous ECG channel and one or more sensing channels which generate intra-cardiac electrogram signals; and,
setting an alarm flag if a programmable number of cross-checks fail.

20. The method of claim 19 wherein the cross-checking of chamber senses includes measurement of intervals between chamber senses in the subcutaneous ECG channel and intra-cardiac sensing channel.

21. The method of claim 13 further comprising detecting excitation current bursts from a minute ventilation sensor in the subcutaneous ECG signal and setting an alarm flag if a programmable number of such bursts fail to be detected.

22. The method of claim 13 further comprising:
detecting body activity with an accelerometer;
sensing minute ventilation with a minute ventilation sensor which outputs bursts of excitation current for measuring trans-thoracic impedance; and,
cross-checking the activity of the accelerometer and minute ventilation sensor and setting an alarm flag if a discrepancy exists.

23. The method of claim 13 further comprising communicating the setting of the alarm flag to a patient management network.

* * * * *